United States Patent [19]
Darlix et al.

[11] Patent Number: 5,747,323
[45] Date of Patent: May 5, 1998

[54] RETROVIRAL VECTORS COMPRISING A VL30-DERIVED PSI REGION

[75] Inventors: Jean-Luc Darlix, Chaponost; Christophe Torrent, Sainte Foy Les Lyon, both of France

[73] Assignee: Institut National de la Sante et de la Recherche Medicale (INSERM), Paris, France

[21] Appl. No.: 301,718

[22] Filed: Sep. 7, 1994

Related U.S. Application Data

[63] Continuation of Ser. No. 999,262, Dec. 31, 1992, abandoned.

[51] Int. Cl.$^6$ ............................ C12N 7/01; C12N 5/10; C07H 21/04
[52] U.S. Cl. .............. 435/235.1; 435/357; 435/367; 435/320.1; 536/24.1
[58] Field of Search ........................ 435/69.1, 172.1, 435/172.3, 320.1, 325, 357, 366, 367; 536/23.1, 24.1; 424/93.2, 93.6

[56] References Cited

U.S. PATENT DOCUMENTS

| | | | |
|---|---|---|---|
| 5,399,346 | 3/1995 | Anderson et al. | 424/93.21 |
| 5,543,328 | 8/1996 | McClelland et al. | 435/320.1 |

OTHER PUBLICATIONS

"Report and Recommendations of the Panel to Assess the NIH Investment in Research on Gene Therapy", Dec. 7, 1995.
Eliot Marshall, "Zero Hype, More Biology Needed for Gene Therapy", Science, vol. 270, 15 Dec. 1995, p. 1751.
Eliot Marshall, "Gene Therapy's Growing Pains", Science, vol. 269, 25 Aug. 1995, pp. 1050–1055.
Dougherty et al. "New Retroviral Helper Cells with Almost No Nucleotide Sequence Homology to Retrovirus Vectus", J. Virol., Jul. 1989, vol. 63, No. 7, pp. 3209–3212.
Yu et al. "Self–inactivating Retroviral Vectors Designed for Transfer of Whole Genes Into Mammalian Cells", PNAS, vol. 83, pp. 3194–3198, May 1986.
Torrent et al., Symposium on Foetal and Neonatal Cell Transplantation and Retroviral Gene Therapy, Annecz, France, Jan. 5–8, 1992.

*Primary Examiner*—David Guzo
*Attorney, Agent, or Firm*—Burns, Doane, Swecker & Mathis, L.L.P.

[57] ABSTRACT

The invention proposes a packaging signal (psi) region of at most 400 nucleotides, capable of promoting encapsidation of a retroviral vector, which is substantially homologous to the 5' end of a murine viral-like cellular sequence of type VL30, as well as a retroviral vector comprising said psi region.

16 Claims, 3 Drawing Sheets

Figure 1

1A : Mo MLV provirus genome

1B : a retroviral vector

1C : a helper provirus

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 400 base pairs
        ( B ) TYPE: nucleic acid
        ( C ) STRANDEDNESS: single
        ( D ) TOPOLOGY: linear     ( i i ) MOLECULE TYPE: RNA (genomic)

( v i ) ORIGINAL SOURCE:
        ( A ) ORGANISM: HaMSV
        IMMEDIATE EXPERIMENTAL SOURCE
        NAME OF PLASMID: pI'-HMSV
        POSITION OF THE SEQUENCE IN
        THE PLASMID: 211 to 611

( i x ) FEATURE:
        ( A ) NAME/KEY: misc_RNA
        ( B ) LOCATION: 1..400
        ( D ) OTHER INFORMATION: from 1 to 400 bp: psi sequence
        PROPERTIES: encapsidation sequence     ( x i ) SEQUENCE DESCRIPTION: SEQ ID NO:1:

```
CCGGCCGGCG  UUUGUCUUGU  CUGUUGUGUC  UUGUCCUGUG  AACGAUCGAU  CAAUAGGCUC    60

AGAUCUGGGG  ACUAUCUGGG  CGGGCCAGAG  AAGGAGCUGA  CGAGCUCGGA  CUUCUCCCCC   120

GCAGCCCUGG  AAGACGUUCC  AAGGGUGGUU  GGAGGAGAGG  GAGAUCCGGA  UCCUUGGCAC   180

CUCCGUCCGU  UUUCGGAGGG  AUCCGCACCC  UUGAUGACUC  CGUCUGAAUU  UUUGGUUUCA   240

GUUUGGUACC  GAAGCUGCGC  GGCGCGCUGC  UUGUUACUUG  UUUGACUGUU  GGAAUUGUUU   300

GUCUUCUUUG  UGACCUGACU  GUGGUUUUCU  GGACGUGUUG  UGUCUGUUAG  UGUCUUUUUG   360

ACUUUUGUUU  CGUGUUUGAA  UUUGGACUGA  CGACUGUGUU                           400
```

RETROVIRAL VECTORS COMPRISING A VL30-DERIVED PSI REGION

This application is a continuation of application Ser. No. 07/999,262, filed Dec. 31, 1992, abandoned.

The invention relates to a retroviral vector which comprises a packaging signal (psi) region derived from a murine viral-like cellular sequence of type VL30. Such a vector is typically designed for use in gene therapy.

Nowadays a wide variety of retroviral vectors have been developed from various retrovirus genomes and are widely used to transfer genes of interest into the cell genomes.

Retrovirus Genomes

Figure 1:
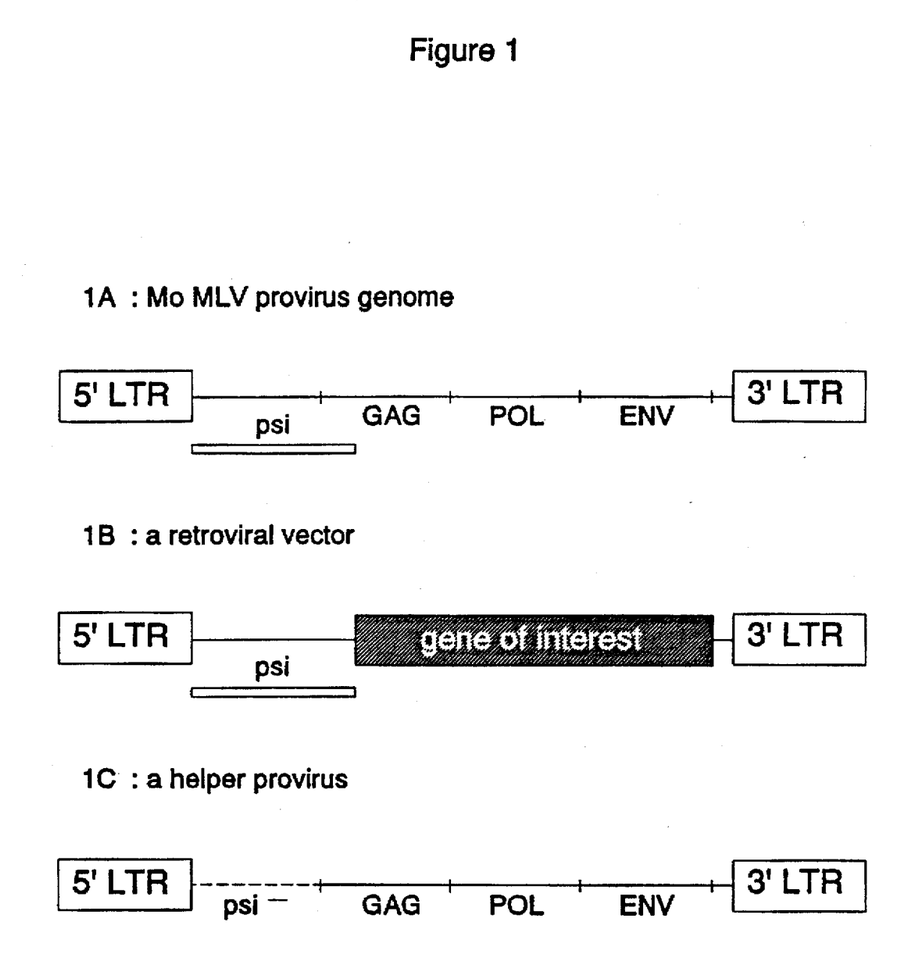
FIG. 1 (Parts A–C) is a schematic representation of a wild type MoMuLV genome (1A), a typical retroviral vector (1B) and a conventional helper provirus (1C).

A retrovirus is a RNA virus, the genome of which typically comprises, as indicated in FIG. 1A:

Three structural genes, gag, pol and env which respectively encode the internal capsid proteins, the reverse transcriptase enzyme and the envelope glycoprotein. This latter is located at the surface of the virus and involved in the host range infectivity. In addition to this, integrase function is provided by the sequence coded by the 3' end of the pol gene.

Cis-acting sequences located at the 5' and 3' ends, also called Long Terminal Repeats (LTRs). The 5' LTR contains promoter sequences and regulatory elements required for the initiation of transcription, whereas the 3' LTR is involved in termination of transcription. Both LTRs also comprise sequences recognized by the integrase.

A packaging signal (psi) region, which is in particular involved in the encapsidation process.

Retroviruses can only replicate through a process of integration of the retroviral genome into the cell chromosomes.

Retroviral Life Cycle

Once the host cells are infected, the viral RNA genome is reverse-transcribed into a double strand DNA molecule, which integrates at random into the cellular genome as a provirus and becomes part of the host genome. The proviral DNA is then transcribed into RNA by the host machinery to produce either the full length viral genome or RNA which is further translated into viral proteins.

Two copies of the viral RNA genome (a dimer) are packaged into a particle. Finally the mature virions bud out of the infected cells, usually with no cellular damage.

This unique mechanism of provirus integration into cellular DNA has been used to incorporate foreign genes in vivo. Retroviral vectors have been developed for this purpose.

Retroviral Vectors

As illustrated in FIG. 1B, retroviral vectors are typically constructed by deleting major parts of the three structural genes of a retroviral genome, whereas the cis-acting elements and the psi region are retained. In other words, retroviral vectors are gag$^-$, pol$^-$ env$^-$ and psi$^+$. These deleted viral sequences may be replaced by a gene of interest. Most of the widely used retroviral vectors are derived from the genome of the Moloney Murine Leukemia Virus (MoMuLV).

In order to be propagated, such a retroviral vector is transfected into a packaging or helper cell line containing integrated copies of a helper provirus, which encodes all the structural proteins necessary for the encapsidation of the recombinant retroviral vector but which is encapsidation-defective. In other words, the helper provirus is gag$^+$, pol$^+$, env$^+$ and psi$^-$. Such a transfection results in the production of virions by encapsidation of the retroviral psi$^+$ genome into a viral particle constructed from the proteins produced from the helper psi$^-$ construct. The virions so-obtained are replication-defective because their genome lacks the genes encoding the structural proteins. They can only infect target cells and integrate in the cell genome but there is no further propagation of the virions.

Conventional packaging cell lines are usually derived from mouse fibroblasts 3T3, in the genome of which has been introduced a helper provirus. A typical helper construct is constituted by a MoMuLV provirus in which the psi region is deleted (FIG. 1C).

Since the MoMuLV envelope glycoprotein is present at the surface of the recombinant retroviral particle, the virions generated by such a conventional cell line have an ecotropic restricted host range infectivity similar to that of MoMuLV. Alternatively, amphotropic helper cell lines have been engineered by replacing the MoMuLV env gene by an amphotropic env gene, such as one derived from the Gibbon ape leukemia virus (GalV). Thus recombinant viruses produced in these amphotropic helper cell lines are able to infect a broad range of mammalian cells including a large variety of human cells such as hematopoietic, skin, muscle or liver cells.

Safety Consideration

However a general drawback of the available retroviral vectors consists in the contamination of the recombinant virus stocks with replication-competent viruses, a safety concern which is unacceptable for human gene therapy.

When a cell contains simultaneously two different but related viral genomes (such as a helper cell containing the helper genome and transfected with the recombinant retroviral vector; these two genomes sharing common regions since they both derive from MoMuLV), heterodimers comprising a genome of each type are likely to occur. Encapsidation of such heterodimers and their subsequent reverse transcription might be responsible for the generation of replication-competent viruses.

There are substantial regions of homology between the retroviral vector and the helper provirus. Such regions include LTRs and the overlap between the psi sequence and the gag gene. Indeed, the MoMuLV psi region, designated hereinafter the endogenous or conventional MoMuLV psi region, is about 800 nucleotides (nt) long and has a 3' end which extends into the gag coding sequence. This sequence is present both in the retroviral vector and the helper provirus. Although the 3' end of the MoMuLV psi region may promote the formation of heterodimers, it has to be maintained in conventional retroviral vectors since it favours the obtention of high virus titers in helper cell lines.

Various solutions have already been proposed to minimize this problem, and include:

- introducing multiples mutations in the 5' and 3' LTRs of the helper DNA construct in order to reduce to a minimum the homology with the recombinant vector, making them more difficult to recombine as described in U.S. Pat. No. 4,861,719 or,
- introducing into the helper cell line the trans-complementation structural viral genes onto two different plasmids so that 3 recombination events (rather than only two) are required to generate replication-competent viruses as described in WO 92/05266.

But so far these alterations have only allowed a reduction of the generation of replication-competent viruses or have resulted in a substantial reduction of the titer of recombinant viruses upon transfection of the retroviral vector into a packaging cell line or a reduced expression of the gene of interest.

Viral-Like Cellular Sequences

The genome of most vertebrates contains endogenous sequences that possess the ability to move from a location to another within the cellular genome. Some of these mobile elements, called retrotransposons, exhibit structural similarities with proviruses. Indeed, they contain inverted repeats at both ends, transpose through RNA intermediates and are capable of random insertion into cellular chromosomes, but otherwise vary in size and coding capacity. The function and the biological significance of these genetic elements are still unknown.

The murine genome contains several families of such mobile elements. Among them, one class of retrotransposons has been characterized: the VL30 sequences, the name of which originates from the fact that they exhibit "Virus-Like" properties and that the corresponding RNAs have a sedimentation coefficient of about 30S. These VL30 RNAs are replication-defective and do not encode any protein.

Some VL30 elements might be transmitted from cell to cell since they can be packaged in the presence of a helper virus. This may promote rare events which could lead to the generation of a virus of a new type, such as the Harvey Murine Sarcoma Virus (HaMSV).

Harvey Murine Sarcoma Virus

Figure 2:
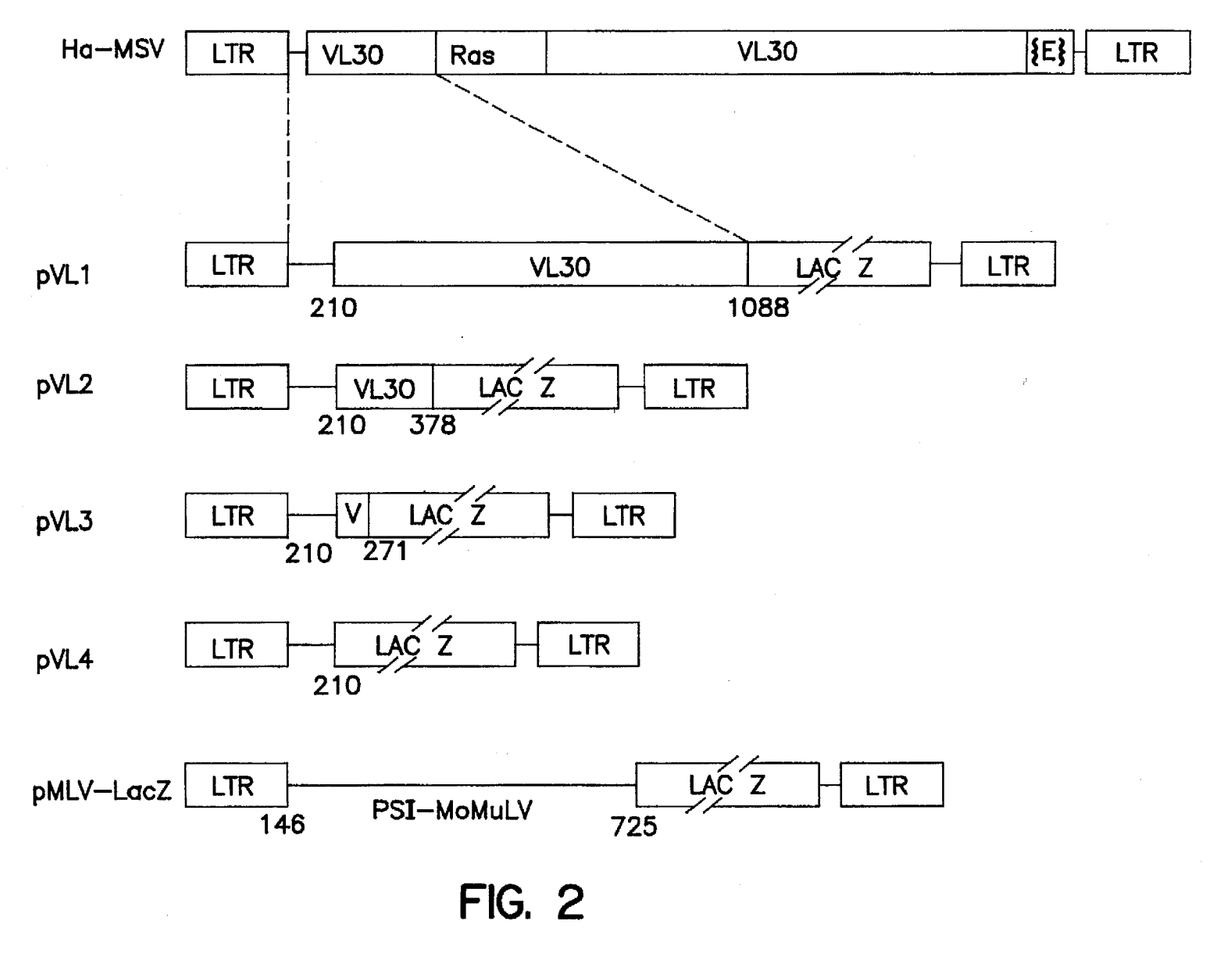
FIG. 2 is a schematic representation of the HaMSV genome and the retroviral vectors carried by the plasmids described in the following example: pVL1 is a positive control comprising the complete VL30-derived psi region of HaMSV; pVL2 and pVL3 are representatives of retroviral vectors according to the invention, which comprise a VL30-derived psi region of respectively 168 and 61nt long; pVL4 is a negative control lacking psi region; pMLV-LacZ is a control comprising a conventional MoMuLV psi sequence. Open boxes represent the various elements combined in constructs and include abbreviations of these elements. HaMSV corresponds to plasmid pT-HMSV. Abbreviations used are as follows: LTR, long terminal repeat; VL30 (or V), sequence derived from a VL30 element; LAC Z, lacZ gene coding for procaryotic β galactosidase; Ras, c-ras sequence integrated in HaMSV; [E], partial sequence of the MoMuLV env gene. Numbers below each construct correspond to nt positions, +1 corresponding to the 5' end of the RNA transcript generated from MoMuLV LTR. In all pVL constructs, LTRs and sequence from positions 146 to 209 are from MoMuLV origin. In pMLV-LacZ, the psi sequence is illustrated by a solid line and extends from positions 146 to 725 of the MoMuLV genome.

The HaMSV genome has a complex origin. It appears to have been generated by multiple recombination events between MoMuLV genome, rat cellular VL30 sequences and rat cellular ras (c-ras) gene. FIG. 2 depicts a schematic representation of a wild type HaMSV genome which contains 5' and 3' LTRs from MoMuLV origin and a rat VL30 element interrupted by a gene coding for the oncogenic protein p21$^{ras}$. In HaMSV, the psi region is constituted by a portion of the rat VL30 sequences (positions 220 to 940; numbering is according to Van Beveren and Hughes, in RNA tumor viruses, R. Weiss, N. Teich, H. Warmus and J. Coffin, 2nd ed., 1984, 2, 928–939, Cold Spring Harbor Laboratory, New York, position +1 corresponds to the 5' end of the RNA transcript) and the HaMSV genome appears to be efficiently packaged into MoMuLV particles.

Use of VL30 Sequence as Candidate for Gene Transfer Vectors

A document of the prior art (WO92/07950) has proposed to use a VL30 retrotransposon for transferring and expressing a gene of interest in a cell or an organism. The gene to be expressed is inserted into a reverse-transcribed VL30 and the resulting vector is transfected into a conventional helper cell line. The recombinant VL30 construct is efficiently packaged into MoMuLV viral particles. The infectious virions generated comprising the VL30 construct might be used to infect selected host cells for a wide variety of applications.

Although considerable progress has been made in the development of retroviral vectors, the need for even more efficient vectors exists, especially in view of a human therapeutic use, which combine critical parameters, such as a high packaging efficiency, generation of high titers of viruses, high expression of the transduced gene as well as the necessary biological safety.

It has now been found that a particular region of a murine viral-like cellular sequence of type VL30 is capable of promoting efficient encapsidation of a retroviral vector. The presence in a retroviral vector of this VL30-derived psi region of a maximum of 400 nt in length, provides for several advantages as compared to the conventional MoMuLV psi region, which are:

(1) efficient encapsidation rates,
(2) high titers of recombinant viruses produced upon transfection into helper cell lines,
(3) possibility of transduction of larger genes of interest.

Furthermore, the VL30-derived psi region does not possess any striking homology with the endogenous MoMuLV psi region. This lack of homology will allow the development of new retroviral vectors with improved biological safety since it greatly reduces, if not prevents, the risk of formation of RNA heterodimers.

Another advantage of this particular psi region is that it does not code for portions of viral proteins which may have deleterious effects in the target cells.

Therefore, the present invention provides for an isolated DNA fragment capable of promoting encapsidation of a retroviral vector and having a psi sequence of at most 400 nucleotides, wherein said psi sequence is substantially homologous to the 5' end of a murine viral-like cellular sequence of type VL30.

By "isolated DNA fragment" it is meant a DNA fragment which is free of or is not associated with any other DNA fragments of a murine virus-like cellular sequence of type VL30.

A DNA fragment according to the invention has a psi sequence substantially as shown in SED ID No: 1, which starts with any one of nucleotides from positions 1 to 10, advantageously from positions 1 to 6 and preferably from positions 1 to 3 and which ends with any one of nucleotides from positions 41 to 400, advantageously from positions 50 to 300 and preferably from positions 55 to 180.

In a preferred embodiment, a DNA fragment according to the invention has a psi sequence substantially as shown in SED ID No: 1, starting with the nucleotide in position 1 and ending with the nucleotide in position 61. This psi sequence retains efficient encapsidation rate as compared to the endogenous MoMuLV psi sequence.

In a particularly preferred embodiment, a DNA fragment according to the invention has a psi sequence substantially as shown in SED ID No: 1, starting with the nucleotide in position 1 and ending with the nucleotide in position 168. This short psi sequence proved to be more efficient than the endogenous MoMuLV psi sequence for encapsidation of a retroviral vector.

The terms "substantially homologous" and "substantially as shown" are used to indicate that psi sequences slighty different from the natural VL30-derived psi sequence are also within the scope of the invention, provided that (i) the substitution, the addition or the deletion of one or several nucleotides does not affect the function of the DNA fragment and,
(ii) it can be recognized that these slighty different psi sequences actually derive from VL30 sequences.

It is usually considered that point (ii) is met when the degree of homology between these slighty different psi sequences and the natural VL30-derived psi sequence of reference is at least 80%, preferably at least 90%. Common variations usually correspond to a homology degree of 97–99%.

According to a second aspect of the present invention, it is provided a retroviral vector comprising (1) a 5' LTR and a 3' LTR derived from a retrovirus, (2) an isolated DNA fragment according to the invention and (3) a DNA fragment of interest, capable of being transcribed into RNA to produce an anti-sense RNA molecule or to further produce a protein of interest upon translation of said RNA. 5' and 3' LTRs may derive from various types of retroviruses. Examples of suitable retroviruses include avian retroviruses such as Avian Erythroblastose Virus (AEV), Avian Leukosis Virus (AVL), Avian Sarcoma Virus (ASV), Spleen Necrosis Virus (SNV) and Rous Sarcoma Virus (RSV), bovine retroviruses, feline retroviruses, murine retroviruses such as Murine Leukemia Virus (MuLV), Friend Murine Leukemia Virus and Murine Sarcoma Virus (MSV) and primate retroviruses. Others suitable retroviruses are well known in the art. A particularly preferred retrovirus is the MoMuLV virus. Thus, retroviral vectors of the invention are preferably engineered from MoMuLV-derived vectors, such as the N2 vector as well as derivatives of this vector.

In the retroviral vector of the invention, the DNA fragment of interest may be any DNA fragment which displays a sequence of cDNA type or genomic DNA or a combination of both types in order to constitute what is commonly called a minigene. The DNA fragment of interest may be any gene of cellular origin, preferably of human origin, or derived from a pathogenic organism.

The DNA fragment of interest may be any DNA fragment capable of being transcribed into an anti-sense RNA, for example a RNA sequence complementary to a pathogenic gene, which is able to form a duplex with the pathogenic transcript in order to inhibit translation into a pathogenic protein. A pathogenic gene is a gene which is not present in mammalian cells, such as genes present in the genome of pathogenic organisms (bacteria, viruses or parasites) or a homologous gene or a mutant homologous gene such as an oncogene, which is present but not normally expressed in healthy mammalian cells and the abnormally-induced expression of which may cause a disease such as a cancer.

Alternatively, the retroviral vector of the invention may comprise a DNA fragment of interest which encodes a protein of interest. Of particular interest are proteins, the absence or altered amount of which or the mutant form of which is associated with a genetic disorder.

The DNA fragment of interest of the invention may encode a mature protein or a precursor. In the first case, the DNA fragment of interest contains a sequence encoding mature protein of interest, allowing the expression of said protein intracellularly. In the latter case, the DNA fragment may additionally include a signal sequence allowing secretion of said protein from the host cell. The DNA fragment of interest may encode chimeric protein resulting from the fusion of sequences of various origins.

Examples of proteins which can be encoded by the DNA fragment of interest include:

cytokines such as interleukins, alpha and gamma-interferon, different types of colony stimulating factors (CSF) and various growth factors, membrane receptors such as various receptors involved in transmitting signals from the cell surface to the nucleus and cellular receptors specifically recognized by pathogenic proteins, enzymes such as ribonucleases and the Herpes Simplex Virus type I (HSV-1) Thymidine Kinase (TK). This latter displays a higher affinity for certain nucleoside analogs, such as acyclovir and gancyclovir, than mammalian TK. These analogs are converted by the viral TK to nucleotide-like precursors which are incorporated into the DNA of replicating cells, thus leading to their death. In presence of such a nucleoside analog, this enzyme allows the specific killing of dividing cells, such as cancerous cells.

inhibitors of an enzyme activity such as α lantitrypsin, tissue plasminogen activator, antithrombin III, protein C and inhibitors of proteases specific to pathogenic organisms, proteins involved in ion channels such as Cystic Fibrosis Transmembrane Conductance Regulator, coagulation factors such as factor VIII, factor IX (FIX) and thrombin, antigenic epitopes such as surface viral proteins and tumoral determinants, immunoglobulin chains, proteins capable of inhibiting the activity of a protein produced by a pathogenic gene such as a tumor-suppressor protein like p53 antigen and, variants of pathogenic proteins with altered properties, such as a mutant of the Human Immunodeficiency Virus (HIV) trans-activator tat protein which is capable of competiting with the wild type polypeptide for binding to its target sequence but which is unable to trans-activate expression of HIV genes.

The DNA fragment of interest can also be mutated in order to express a variant of a protein of interest with improved or altered biological properties, such as a variant of α1AT in which the active site residue Met in position 358 has been replaced by a leucine. Such a variant α1AT (Leu$^{358}$) should allow the inhibitor protein to be functional in oxidative conditions, such as in inflammation conditions.

The DNA fragment of interest may be expressed under the control of the viral 5' LTR. Alternatively, the retroviral vector may comprise an additional promoter region located upstream from the DNA fragment of interest. In the context of the invention, the term "internal promoter region" means any transcriptional control element involved in gene expression in a host cell, such as promoters, enhancers, Upstream Activating Sequence (UAS) or Upstream Repressing Sequence (URS). They may be of cellular or viral origin. These transcriptional control elements may be a combination of such elements of various origin. Such transcriptional control elements are well-known in the art and a suitable promoter region may be linked upstream from the DNA fragment of interest in an operative way by conventional recombinant DNA techniques.

The internal promoter region may be a constitutive promoter region allowing high expression of the gene of interest. Examples of such ubiquitous promoter regions are, without limitation, the SV40 (Simian Virus 40) promoter or the hydroxy-Methyl-Glutaryl-coenzyme A reductase (HMG) gene promoter.

The term "internal promoter region" also includes a responsive promoter which confers tissue or event-specific expression of the DNA fragment of interest. Examples of tissue-specific promoters are, without limitation, the α1AT gene promoter which confers marked specificity to liver, the hepatocyte-specific FIX gene promoter, the immunoglobulin gene promoter which targets expression to B lymphocytes, the lung-surfactant gene promoter which directs expression to pulmonary cells. Event-specific promoters may be used to permit expression of the gene of interest at the appropriate moment. Examples of such regulated promoters are, without limitation, cell-cycle promoters or a growth-hormone responsive promoter region which may allow expression of the gene of interest more specifically in tumoral cells since said cells are known to produce high amount of growth factors.

It is also in the scope of the invention that the retroviral vector of the invention may additionally comprise a DNA fragment encoding a selection marker enabling detection and isolation of the transformed host cells harboring such a retroviral vector. In the context of the present invention, the DNA fragment coding for a selection marker may be under the transcriptional control of the promoter driving expression of the gene of interest, resulting in a bicistronic transcript or under the control of an additional promoter region inserted upstream from said DNA fragment. The dominant selection genes are numerous, for example neo gene conferring resistance to antibiotic G418, dihydrofolate reductase (dhfr) gene or xanthine phosphoribosyl transferase (gpt) gene allowing selection in the presence of mycophenolic acid and xanthine.

According to a third aspect of the invention, it is provided infectious viral particles generated upon transfection of a recombinant retroviral vector of the invention into a packaging cell line. Preferred packaging cell lines are either ecotopic cell lines such as CRE (Danos and Mulligan, 1988, Proc. Natl. Acad. Sci. USA, 85, 6460–6464) or GPE+86 (Markowitz et al., 1988, J. Virol., 62, 1120–1124) or amphotropic cell lines such as PG13 (Miller et al., 1991, J. Virol., 65, 2220–2224) or Psi Env-am (Hartley and Rowe, 1976, J. Virol., 19, 19–25). Other suitable helper cell lines are well-known in the art. The recombinant infectious virus particles produced in an amphotropic cell line are able to infect a wide variety of human cells including, without limitation, epithelial cells, hepatocytes, lymphocytes, fibroblasts. Of particular interest are hematopoietic cells.

According to a fourth aspect of the invention, it is also provided a method for preparing an infectious viral particle of the invention. Such a method comprises the act of (1) introducing a recombinant retroviral vector of the invention into a packaging cell line, (2) culturing said packaging cell line under suitable conditions permitting production of the said viral particle and (3) recovering the resulting viral particle from cell culture supernatant.

According to a fifth aspect of the invention, it is also provided a mammalian cell comprising a retroviral vector of the invention. Such a mammalian cell may be generated either by infection of a target cell with an infectious viral particle of the invention or by transfection of a retroviral vector of the invention into a helper cell line.

A retroviral vector or an infectious particle as well as a mammalian cell of the invention may be applied in the prevention or treatment of various diseases, as a vaccine or a therapeutic agent.

It is also in the scope of the invention to provide for a pharmaceutical composition comprising a therapeutically or prophylactically effective amount of a retroviral vector or an infectious particle as well as a mammalian cell of the invention as a therapeutic agent. Such a pharmaceutical composition may be produced in a conventional manner. In particular, a retroviral vector or an infectious particle as well as a mammalian cell of invention may be combined with appropriate substances well known in the art, such as a carrier, diluent, adjuvant or excipient. The particular formulation of the pharmaceutical composition depends on various parameters, for example the protein of interest to be expressed, the desired site of action, the method of administration and the subject to be treated. Such a formulation can be determined by those skilled in the art and by conventional knowledge.

In a last embodiment of the invention, it is also provided a method of treating a genetic disorder or a disease induced by any pathogenic gene, such as cancer or a virally-induced disease, which comprises administering a therapeutically effective amount of a retroviral vector or an infectious particle as well as a mammalian cell of the invention to a subject in need of a treatment.

These and other advantages of the subject invention will be apparent from the following example and attached drawings. These embodiments do not represent the full scope of the invention.

The present invention will now be illustrated in the following and non limiting example.

EXAMPLE

Retroviral Vectors Constructions

For the purpose of the present invention, retroviral vectors derived from MoMuLV and comprising either a conventional MoMuLV psi sequence (pMLV-LacZ) or a VL30-derived psi region (pVL1 comprising the complete VL30-derived psi region of HaMSV used as a control, pVL2 comprising a 168nt VL30-derived psi region and pVL3 comprising a 61nt VL30-derived psi region) are constructed as well as a negative control lacking a psi sequence (pVL4). The gene of interest expressed is the bacterial lacZ gene coding for β galactosidase. Expression of lacZ gene is evaluated by X-gal staining.

All constructions are made by using standard recombinant DNA techniques as described in T. Maniatis et al., Molecular cloning: a laboratory manuel, Cold Spring Harbor, N.Y., 1982. *Escherichia coil* (*E. coli*) HB101 is used for plasmid amplification. The different vectors described hereinafter are constructed from plasmids which have been reported previously: (1) pMLVK which includes the proviral genome of MoMuLV (Miller and Verma, 1984, J. Virol., 49, 214–222; Prats et al., 1990, J. Virol., 64, 774–783), (2) pI'-HMSV comprising the complete proviral genome of HaMSV in which nt 940 to 1088 are replaced by equivalent sequence of cellular ras gene c-ras (Velu et al., 1989, J. Virol., 63, 1384–1392) and nt 339 and 384 have been substituted respectively by a G and a U as compared to the published sequence and (3) pCH110 (Pharmacia) comprising the bacterial lacZ gene. A schema of the different constructions is shown in FIG. 2 as well as the HaMSV genome.

Construction of pMLV-LacZ

The pMLV-LacZ vector results from the ligation of the three following fragments:
(1) a ClaI-blunt-ended BstEII fragment, isolated from pMLVK partially digested with ClaI and BstEII. This fragment includes the MoMuLV 5' LTR together with the psi region up to nt 725,
(2) a ClaI-blunt-ended AatII fragment purified from pMLVK partially digested with both restriction enzymes. This fragment contains the MoMuLV 3' LTR and the pBR322-derived origin of replication of E. coli and the β lactamase gene conferring resistance to ampicilin (Amp) and,
(3) a StuI-SmaI fragment encompassing the lacZ gene and generated as follows: pCH110 is cut with HindIII and BamHI. The 3.7 kb fragment is purified and subsequently ligated with two synthetic linkers. The linker L1 is cloned into the HindIII site of the LacZ fragment and comprises from 5' to 3' a StuI, a BamHI, a XhoI, a BglII and a SnaBI and a HindIII restriction site. The linker L2, comprising from 5' to 3' a BamHI, a EcoRI and a SmaI site, is inserted into the BamHI site of the LacZ fragment. The mixture is then digested with StuI and SmaI restriction sites and the LacZ insert purified on agarose gel.

Following transformation of the resulting ligation mixture into a E. coli HB101 recA⁻ strain, the Amp resistant clones are analyzed by restriction digestion to select the clones displaying the LacZ gene in the appropriate orientation relatively to the MoMuLV 5' LTR. The resulting plasmid is designated pMLV-LacZ and exhibits the 5' LTR of MoMuLV, the MoMuLV psi sequence up to nt 725, the bacterial lacZ gene followed by the 3' LTR of MoMuLV.

Construction of p VL1

A XbaI-HindIII DNA fragment isolated from pI'-HMSV (positions -151 to 1088) is introduced into pMLV-LacZ digested with HindIII and partially digested with XbaI (cleavage of the XbaI site located in the 5' LTR) to give pVL1, which comprises in sequence the 5' LTR of MoMuLV up to position 210, the VL30-derived psi region of HaMSV (positions 210 to 1088), the lacZ gene and the MoMuLV 3' LTR.

Construction of p VL2

A XbaI-BamHI DNA fragment isolated from pI' HMSV (positions -151 to 378) is inserted in pMLV-LacZ digested with BglII and partially with XbaI. The resulting plasmid pVL2 is similar to pVL1 with the exception that the psi region lies from nt 210 to 378 of HaMSV.

Construction of pVL3

A XhoI-BglII fragment isolated from pVL2 is ligated to pMLV-LacZ cut by XhoI and BglII. The resulting plasmid pVL3 comprises the MoMuLV 5' LTR up to nt 210, a psi region of 61nt (positions 210 to 271) from HaMSV origin, the lacZ gene and the MoMuLV 3' LTR.

Construction of pVL4

Deletion of the psi region is performed by NaeI-BglII digestion of pVL1 followed by treatment with the Klenow fragment of the E. coli polymerase I and religation. This plasmid constitutes a negative control lacking a psi encapsidation sequence.

Figure 3:
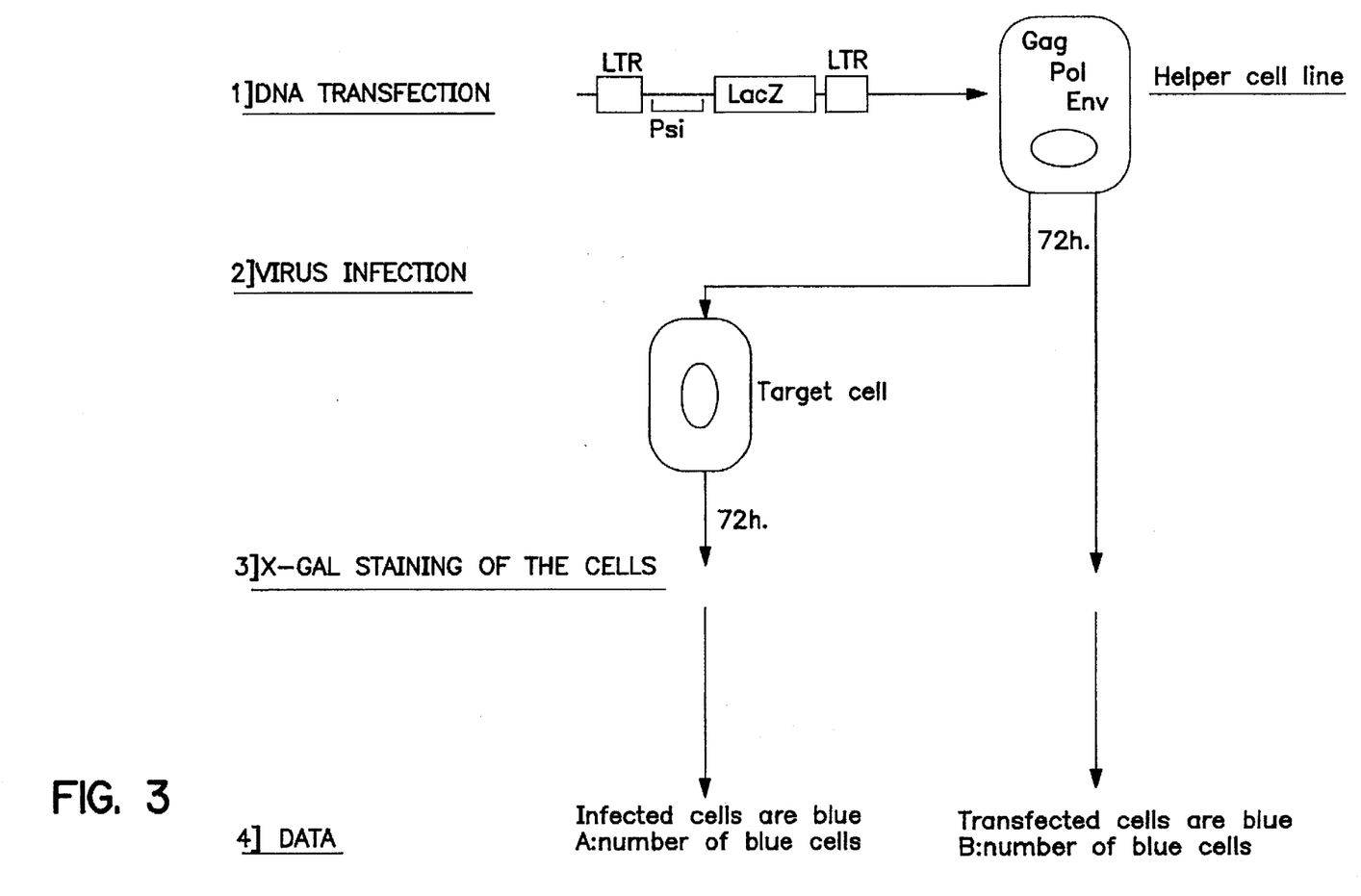
FIG. 3 is a schematic representation of the general method allowing the measurement of the retroviral vector packaging efficiency.

Determination of the Relative Encapsidation Efficiency of the Vectors Described Herein The general method for evaluating the encapsidation efficiency of all retroviral vectors described herein, is depicted in FIG. 3. This estimation is performed both by transient and long term expression analysis. Three different helper cell lines are transfected by plasmid DNA comprising one of the retroviral vectors described above. The three different helper cell lines consist in the ecotropic 3T3 derived CRE and GPE+86 and the amphotropic PG 13. Three days after transfection, virions present in the culture supernatant of helper cell lines are used to infect host cells. Infectivity is estimated using either mouse 3T3 cells for virions produced in ecotropic cell lines or human HeLa cells for those produced in amphotropic cells. Three days later, expression of the lacZ gene is evaluated by X-gal (blue) staining of the infected as well as transfected cells. Encapsidation efficiency of each recombinant viral genome is given by the ratio of the stained infected cells versus transfected helper cells. Values obtained with pMLV-LacZ have been normalized to 100%.

Generation of Recombinant Virions by the Helper Cells

DNA transfections of the three helper cell lines are performed by a slighty modified calcium phosphate procedure according to Chen and Okyama, 1987, Mol. Cell Biol., 7, 2745–2753. In addition to the Ca-phosphate mediated transfection technique, others protocols for introducing nucleic acids into cells may be employed such as DEAE-dextran technique, electroporation, osmotic shock based methods. The DNA constructs may also be micro-injected into a selectionned cell.

Ecotropic helper cells CRE and GP+86 are cultured in Dulbecco's Modified Eagle's Medium (DMEM) supplemented with 10% of New Born Calf Serum (NBCS). Amphotropic PG13 cells are grown in DMEM containing 10% of Fetal Calf Serum (FCS). The cells are maintained at 37° C. and in presence of 5% $CO_2$. The cells are seeded at $5 \times 10^5$ cells per 100 mm dish, 24 hours prior to transfection. In transient experiments, 20 µg of plasmid (pMLV-LacZ, pVL1, pVL2, pVL3 or pVL4) are mixed to 0.5 ml of 0.25M $CaCl_2$. The mixture is added drop by drop in 0.5 ml of 2×HBS (50 mM Hepes; 280 mM NaCl; 1.5 mM $Na_2HPO_4$; pH 6.95) and incubated at room temperature for 30 minutes. DNA-Ca phosphate is then settled drop by drop on the cultured cells. Transfected cells are cultured for 24 hours at 35° C. in 3% $CO_2$ and washed twice with new medium before being grown at 37° C. in 5% $CO_2$ for an extra day.

For stable cell line establishment, cells are co-transfected with 18 µg of each plasmid and 2 µg of pSV2neo (Southern and Berg, 1982, J. Mol. Appl. Genet., 1, 327) conferring G418 resistance selection. After 2 days of culturing, cells are diluted (1:20) and grown in selective medium containing 800 µg ml⁻¹ of G418 (Geniticin, Gibco) for 2 weeks.

The recombinant virions are harvested from supernatants resulting from transient or long term transfected cells cultured in fresh medium for 48 hours. Such a medium is centrifuged at 400 rpm for 20 minutes at 4° C. to remove cells and cellular debris.

Virus Infection of Host Cells

Aliquots of supernatant are then tested for the presence of ecotropic or amphotropic recombinant virions using respectively mouse fibroblasts 3T3 NIH and HeLa cells as host cells. The 3T3 NIH cells are cultured in DMEM 5% NBCS at 37° C. in presence of 5% $CO_2$, whereas HeLa cells are grown in DMEM 5% FCS.

On day one, host cells to be infected are plated at $5 \times 10^5$ cells per 60 mm dish. On day two, cells are grown in fresh culture medium containing Polybrene (8 μg $ml^{-1}$) and infected with various dilutions of viral supernatants to be tested. On day three, infected cells are trypsinated and diluted to 1:10 in appropriate medium (non selective in case of transient experiment or selective in case of long term expression) and are grown for at least 48 hours before assessing expression of the gene of interest. LacZ gene expression is monitored by histochemistry.

Measurement of β Galactosidase Activity in Transfected and Infected Cells

Cells are washed in PBS 1×(1.06 mM $KH_2PO_4$; 154 mM NaCl; 5.6 mM $Na_2HPO_4$) and then fixed by 10 minutes incubation at 20° C. in the following solution (2% formaldehyde; 0.2% glutaraldehyde in PBS 1×). After 2 additional washings, X-gal staining is performed at 37° C. by immerging the fixed cells in the following mixture (1 mg $ml^{-1}$ X-gal; 4 mM $Fe^{2+}$ and $Fe^{3+}$ cyanide of potassium; 0.2 mM $MgCl_2$ in PBS 1×). In both cases, transient and long term experiments, the packaging efficiency of each vector candidate is calculated by the following formula: (A:B)×100, where A is the number of blue cells in virion infected cells and B is the number of blue cells in the corresponding transfected cells.

Packaging efficiencies mediated by pVL vectors comprising a VL30-derived psi region relatively to pMLV-LacZ as a control are presented in Table 1 which gives the results obtained following transient transfections of the three different helper cell lines and long term experiments. The values obtained with pMLV-LacZ are normalized to 100%. Packaging ratios measured with pVL vectors are calculated relatively to 100%.

TABLE 1

| DNA vectors | | PACKAGING RATIOS (%) | | | | | |
|---|---|---|---|---|---|---|---|
| | | Transient expression | | | Stable transformants | | |
| | | CRE | GP + E86 | PG13 | CRE | GP + E86 | PG13 |
| VL30 | | | | | | | |
| pVL1 210 | 1088 | 175 | 140 | 230 | 210 | 185 | 205 |
| pVL2 210 | 378 | 140 | 125 | 170 | 170 | 150 | 190 |
| pVL3 210 | 271 | 80 | 110 | 125 | 115 | 125 | 135 |
| pVL4 | | 3 | 1 | 4 | 2 | 0 | 4 |
| PSI-MoMuLV pMLV-LacZ | | 100 | 100 | 100 | 100 | 100 | 100 |

From these data, it can be seen that packaging ratios induced by a complete VL30-derived psi region of HaMSV (positions 210 to 1088) (pVL1), a 168nt VL30-derived psi region (pVL2), and a 61nt VL30-derived psi region (pVL3) are respectively 140 to 230%, 125 to 190% and 80 to 135% in comparison to pMLV-LacZ according to helper cell lines. Without a psi sequence (pVL4), packaging is unefficient (0 to 4%).

Thus, the complete VL30-derived psi region of HaMSV is about 2 fold more efficient than the reference MoMuLV psi region in promoting encapsidation of RNA genomes. These data also reveal that a short VL30-derived psi region of 168nt as found in pVL2 (positions 210 to 378) still remains more efficient than the conventional MoMuLV psi sequence. Further deletion of a VL30 psi region up to position 272 (pVL3) preserves a similar encapsidation rate as that obtained with the reference MoMuLV psi sequence.

Thus, to ensure a packaging efficiency at least similar to that obtained with endogenous MoMuLV psi sequence, a VL30-derived psi sequence of about 41 to 400nt is required.

Absence of Replication-Competent Viruses in Helper Cell Lines Transfected With pVL Vectors To look for the possible generation of replication-competent viruses, long term established helper cell lines producing pMLV-LacZ, pVL1 or pVL2 are cultured for several weeks. Culture supernatants derived from these helper lines are used to repetitively infect host cells (3T3 or HeLa cells) at one week intervals for 2 months. The presence of replication-competent viruses in culture media is assayed by the determination of reverse transcriptase activity according to the method described in Goff et al., 1981, J. Virol., 38, 239–248. The assay is performed on 30 μl of culture medium added to 10 μl of RT×5 buffer (250 mM Tris-HCl pH 8.3; 100 mM DTT; 300 mM NaCl; 0.25 NP40). 10μ1 of mix RT (0.01 mM dTTP; 25 mg/ml polyA oligo dT; 1.5 mM $MnCl_2$; 1μCi dTTP $^{32}P$) is added to the resulting mixture and incubated at 37° C. for 2 hours. The reaction is then filtered on 0.45μm DEAE membranes. The membranes are washed 2 times in 2×SSC (300 mM NaCl, 30 mM $C_6H_5Na_3O_7$, pH7) and exposed for radioactivity detection.

In order to allow rare events to be detected, the sensibility of this assay could be enhanced by a concentration step of the virus containing medium. Viral particles are pelleted after 1 hour centrifugation at 30,000 rpm at 4° C. of 2 ml of culture supernatant. The pellet is resuspended in 40 μl of RT×5 buffer and tested for reverse transcriptase activity according to the method described above.

As a control, medium samples from helper cells transfected with retroviral vectors of the invention exhibit a very important reverse transcriptase activity, indicating the presence of recombinant viruses as expected. After repeated infections of host cells, the presence of replication-competent viruses is once observed in medium samples resulting from the infection of host cells by CRE produced pMLV-LacZ virions whereas replication-competent virions could not be detected in samples deriving from stable cell lines transformed with pVL1 or pVL2 even upon serial infections and cell passages. Theses data indicate that VL30-derived psi region does not induce recombination events between the corresponding retroviral vector and the helper genome and subsequently reduces if not prevents formation of replication- competent viruses.

It can be concluded that the substitution in a retroviral vector of the MoMuLV psi sequence by a VL30-derived psi region, especially a 168 nt region (positions 210 to 378), presents numerous advantages. This VL30 psi region is able (1) to promote RNA packaging with high efficiency, (2) to produce high titers of recombinant viruses upon transfection into helper cell lines, and (3) to accomodate larger gene(s) of interest. Furthermore, the presence of a VL30- derived psi region in retroviral vectors should greatly reduce the risk of production of replication-competent viruses due to a limitation of homology regions with helper genomes. Another advantage of the present invention is that the presence of a psi sequence according to the invention also affects translation of the gene of interest. Indeed, Prats (1988, thesis, University of Toulouse, France) noticed that translation efficiency of gag gene was reduced when the size of MoMuLV leader sequence increases, probably because of a strong secondary structure. Thus a short psi encapsidation sequence should insure an efficient translation of genes of interest.

While the present invention has been described with preferred embodiments and illustrative examples, those skilled in the art after reading the foregoing specification will be able to make changes, alterations, substitutions and equivalents to products and methods described herein.

the nucleotides in positions 1–10 and ending at one of the nucleotides in positions 41–400.

2. The DNA fragment of claim 1, wherein said fragment of SEQ ID NO: 1 consists of a fragment beginning with one of the nucleotides in positions 1–6 and ending with one of the nucleotides in positions 50–300.

3. The DNA fragment according to claim 1, wherein said fragment of SEQ ID NO.: 1 consists of a fragment beginning with one of the nucleotides in positions 1–3 and ending with one of the nucleotides in positions 55–180.

4. The DNA fragment according to claim 1, wherein said psi sequence consists of the nucleotide sequence of SEQ ID NO.: 1 beginning with the nucleotide in position 1 and ending with the nucleotide in position 400.

5. The DNA fragment according to claim 1, wherein said psi sequence consists of a fragment of the nucleotide sequence of SEQ ID NO.: 1 starting with the nucleotide in position 1 and ending with the nucleotide in position 168.

6. The DNA fragment according to claim 1, wherein said psi sequence consists of a fragment of the nucleotide

---

---

We claim:

1. An isolated DNA fragment which promotes encapsidation of a retroviral vector, and which has a psi sequence of at most 400 nucleotides, wherein said psi sequence consists of a fragment of SEQ ID NO: 1 beginning at one of sequence of SEQ ID NO.: 1, starting with the nucleotide in position 1 and ending with the nucleotide in position 61.

7. A retroviral vector comprising
   (1) a 5' LTR and a 3' LTR derived from a retrovirus,
   (2) an isolated DNA fragment according to any one of claims 1–6 and (3) a DNA fragment of interest, capable of being transcribed into RNA to produce an antisense RNA or to produce a protein of interest upon translation of said RNA.

8. A retroviral vector according to claim 7, which further comprises an internal promoter region which promotes transcription of said DNA fragment of interest.

9. An infectious viral particle generated from the retroviral vector according to claim 7.

10. A method for preparing an infectious viral particle which comprises:

(1) introducing a recombinant retroviral vector according to claim 7 into a packaging cell line, (2) culturing said packaging cell line under suitable conditions permitting production of said viral particle and, (3) recovering said viral particle from the cell culture supernatant.

11. A mammalian cell transformed with a retroviral vector according to claim 7.

12. A composition of matter comprising a retroviral vector according to claim 7 and a carrier therefor.

13. A mammalian cell infected with the infectious viral particle according to claim 9.

14. A composition of matter comprising an infectious viral particle according to claim 9 and a carrier therefor.

15. A composition of matter comprising a mammalian cell according to claim 13 and a carrier therefor.

16. A composition of matter comprising a mammalian cell according to claim 11 and a carrier therefor.

* * * * *